US007482444B2

(12) United States Patent
Hovinen

(10) Patent No.: US 7,482,444 B2
(45) Date of Patent: Jan. 27, 2009

(54) TERMINATING SUBSTRATES FOR DNA POLYMERASES

(75) Inventor: Jari Hovinen, Raisio (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 11/710,470

(22) Filed: Feb. 26, 2007

(65) Prior Publication Data

US 2007/0248973 A1 Oct. 25, 2007

Related U.S. Application Data

(60) Provisional application No. 60/781,380, filed on Mar. 13, 2006.

(51) Int. Cl.
| C07H 19/04 | (2006.01) |
| C07H 21/00 | (2006.01) |
| C07H 21/02 | (2006.01) |
| C12P 19/34 | (2006.01) |
| C12Q 1/68 | (2006.01) |

(52) U.S. Cl. .................... 536/26.6; 536/23.1; 536/24.3; 536/24.33; 435/6; 435/91.1

(58) Field of Classification Search ...................... 435/6, 435/91.1; 536/23.1, 24.3, 24.33, 26.6
See application file for complete search history.

(56) References Cited

U.S. PATENT DOCUMENTS

| 4,459,186 | A | 7/1984 | Malloy et al. |
| 4,565,790 | A | 1/1986 | Hemmilä |
| 4,670,572 | A | 6/1987 | Hinshaw et al. |
| 4,761,481 | A | 8/1988 | Hale et al. |
| 4,772,563 | A | 9/1988 | Evangelista et al. |
| 4,794,191 | A | 12/1988 | Hinshaw et al. |
| 4,801,722 | A | 1/1989 | Hinshaw et al. |
| 4,808,541 | A | 2/1989 | Mikola et al. |
| 4,859,777 | A | 8/1989 | Toner |
| 4,920,195 | A | 4/1990 | Kankare et al. |
| 4,927,923 | A | 5/1990 | Mathis et al. |
| 5,032,677 | A | 7/1991 | Hale et al. |
| 5,055,578 | A | 10/1991 | Hale et al. |
| 5,202,423 | A | 4/1993 | Kankare et al. |
| 5,216,134 | A | 6/1993 | Mukkala et al. |
| 5,262,526 | A | 11/1993 | Sasamoto et al. |
| 5,324,825 | A | 6/1994 | Kankare et al. |
| 5,373,093 | A | 12/1994 | Vallarino et al. |
| 5,571,897 | A | 11/1996 | Takalo et al. |
| 5,798,210 | A | 8/1998 | Canard et al. |
| 5,859,215 | A | 1/1999 | Rodríguez-Ubis et al. |
| 6,127,529 | A | 10/2000 | Kwiatkowski et al. |
| 6,255,475 | B1 | 7/2001 | Kwiatkowski |
| 2005/0084451 | A1 | 4/2005 | Hovinen et al. |
| 2005/0181393 | A1 | 8/2005 | Hovinen et al. |

FOREIGN PATENT DOCUMENTS

| EP | 0 139 675 B1 | 1/1987 |
| EP | 0 251 786 A2 | 1/1988 |
| EP | 0 251 786 A3 | 1/1988 |
| EP | 0 298 939 A1 | 1/1989 |
| EP | 0 298 939 B1 | 1/1989 |
| EP | 0 340 675 A2 | 11/1989 |
| EP | 0 340 675 A3 | 11/1989 |
| EP | 0 493 745 A1 | 7/1992 |
| EP | 0 369 000 B1 | 4/1999 |
| EP | 0 770 610 B1 | 7/2005 |
| FI | 20065030 | 1/2006 |
| IT | 1 235 668 | 9/1992 |
| WO | 90/00623 A1 | 1/1990 |
| WO | 93/05049 A1 | 3/1993 |
| WO | 93/11433 A1 | 6/1993 |
| WO | 03/076939 A1 | 9/2003 |

OTHER PUBLICATIONS

Sanger, F., et al., "*DNA Sequencing with Chain-Terminating Inhibitors*", Proc. Natl. Acad. Sci. USA, Dec. 1977, pp. 5463-5467, vol. 74, No. 12, Biochemistry, National Academy of Sciences, Washington, DC, USA.

Hunkapiller, T., et al., "*Large-Scale and Automated DNA Sequence Determination*", Science (Articles), Oct. 4, 1991, pp. 59-67, vol. 254, Amer. Assn. for the Advancement of Science, Washington, DC, USA.

Smith, Lloyd M., et al., "*The synthesis of oligonucleotides containing an aliphatic amino group at the 5' terminus: synthesis of fluorescent DNA primers for use in DNA sequence analysis*", Nucleic Acids Research, 1985, pp. 2399-2412, vol. 13, No. 7, IRL Press Limited, Oxford, England.

Smith, Lloyd M., et al., "*Fluorescence detection in automated DNA sequence analysis*", Nature, Jun. 12, 1986, pp. 674-679, vol. 321, Nature Publishing Group, London, England.

Prober, James M., et al., "*A System for Rapid DNA Sequencing with Fluorescent Chain-Terminating Dideoxynucleotides*", Science (Research Articles), Oct. 16, 1987, pp. 336-341, vol. 238, Amer. Assn. for the Advancement of Science, Washington, DC, USA.

Lee, Linda G., et al., "*DNA sequencing with dye-labeled terminators and T7 DNA polymerase: effect of dyes and dNTPs on incorporation of dye-terminators and probability analysis of termination fragments*", Nucleic Acids Research, 1992, pp. 2471-2483, vol. 20, No. 10, Oxford University Press, Oxford, England.

Fitzgerald, Michael C., et al., "*The Analysis of Mock DNA Sequencing Reactions Using Matrix-assisted Laser Desorption/Ionization Mass Spectrometry*", Rapid Communications in Mass Spectrometry, 1993, pp. 895-897, vol. 7, John Wiley & Sons, Ltd., USA.

Chidgeavadze, Z.G., et al., "*2',3'-Dideoxy-3' aminonucleoside 5'-triphosphates are the terminators of DNA synthesis catalyzed by DNA polymerases*", Nucleic Acids Research, 1984, pp. 1671-1686, vol. 12, No. 3, IRL Press Limited, Oxford, England.

Herrlein, Mathias K., et al., "*3'-Amino-Modified Nucleotides Useful as Potent Chain Terminators for Current DNA Sequencing Methods*", Helvetica Chimica Acta, 1994, pp. 586-596, vol. 77, Verlag Helvetica Chimica Acta, Basel, CH.

(Continued)

*Primary Examiner*—Jezia Riley
(74) *Attorney, Agent, or Firm*—Buchanan Ingersoll & Rooney PC

(57) ABSTRACT

This invention concerns novel terminating substrates for DNA polymerases. The substrates are nucleoside triphosphates labeled with lanthanide chelates.

9 Claims, No Drawings

OTHER PUBLICATIONS

Alexandrova, L.A., et al., "*Nucleoside 5'Triphosphates with Reporter Groups in 2'-Position of Sugar Moiety or in Base as Substrates of DNA Polymerases*", Collect. Czech. Chem. Commun. (Special Issue), 1993, pp. 113-115, vol. 58, Institute of Organic Chem. & Biochem., Acad. Of Sciences of the Czech Republic, Prague, CZ.

Hovinen, Jari, et al., "*Synthesis of 3'-O-(ω-Aminoalkoxymethyl)thymidine 5'-Triphosphates, Terminators of DNA Synthesis that Enable 3'-Labelling*", J. Chem. Soc. Perkin Trans. 1, 1994, pp. 211-217, Royal Society of Chemistry, London, England.

Syvänen, Ann-Christine, et al., "*A Primer-Guided Nucleotide Incorporation Assay in the Genotying of Apoliprotein E*", Genomics, 1990, pp. 684-692, vol. 8, Academic Press, Inc., San Diego, CA, USA.

Jalanko, Anu, et al., "*Screening for Defined Cystic Fibrosis Mutations by Solid-Phase Minisequencing*", Clinical Chemistry, 1992, pp. 39-43, vol. 38, No. 1, American Association for Clinical Chemistry, USA.

Hemmilä, Ilkka, et al., "*Europium as a Label in Time-Resolved Immunofluorometric Assays*", Analytical Biochemistry, 1984, pp. 335-343, Academic Press, Inc., Orlando, FL, USA.

Hemmilä, Ilkka, et al., "*Time-Resolution in Fluorometry Technologies, Labels, and Applications in Bioanalytical Assays*", Critical Reviews in Clinical Laboratory Sciences, 2001, pp. 441-519, vol. 38, No. 6, CRC Press LLC, Boca Raton, FL, USA.

Remuiñán, Modesto, J., et al., "*Synthesis and Luminescence Properties of Europium (III) and Terbium (III) Complexes with Polyacid Chelates Derived from 2,6-Bis(N-pyrazolyl)pyridine[1]*", J. Chem. Soc. Perkin Trans. 2, 1993, pp. 1099-1102, Royal Society of Chemistry, London, England.

International Search Report issued in corresponding International Patent Application No. PCT/FI2007/050127, National Board of Patents and Registration of Finland, Helsinki, FI, 2007.

TERMINATING SUBSTRATES FOR DNA POLYMERASES

FIELD OF THE INVENTION

This invention relates to novel derivatives of labeled nucleoside triphosphates suitable for DNA sequencing.

BACKGROUND OF THE INVENTION

The publications and other materials used herein to illuminate the background of the invention, and in particular, cases to provide additional details respecting the practice, are incorporated by reference.

In the Sanger's sequencing method DNA fragments are synthesised by DNA polymerase which incorporates deoxynucleotide monomers into a polymeric complementary copy of a template DNA strand. An oligonucleotide primer is used to initiate the synthesis of the new DNA stand from the template DNA at a single specific location (Sanger, F., Nicken, S., Coulson, A. R., 1977, PNAS, 74, 5463). Four separate reactions are performed, each containing a carefully controlled ratio of one particular 2',3'-dideoxynucleoside 5'-triphosphate (ddNTP) to the corresponding 2'-deoxynucleoside 5'-triphosphate (dNTP), and the other dNTPs. Once incorporated into a growing DNA strand, the dideoxynucleotide is not able to form a phosphodiester bond with the next incoming dNTP, and the growth of that particular DNA chain stops. Thus, a series of strands is obtained, the lengths of which depend on the location of ddNTP.

In order to detect these oligomers, each fragment must be labelled in some manner. Traditionally, labelling has been accomplished with radioisotopes, such as $^{32}p$ or $^{35}S$ prior of during the polymerase reaction, i.e. using either a radioisotopically labelled primer of dNTPs. Although the radioactive detection is very sensitive, it has intrinsic hazard, expense and problems associated with the short half-lives of the radioactive isotopes commonly used.

Three different methods can be used to avoid radioactive detection:

(i) the use of a primer labelled with a detectable group, such as a chemiluminescent dye (Hunkapiller, T., Kaiser, R. J., Koop, B. F., Hood, K. L., 1991, Science, 254, 59, Smith, L. M., Fung, S, Hunkapiller, M. W., Hunkapiller, T. J., Hood, L. E., 1985, Nucleic Acids Res., 13, 2399, Smith, L. M., Sanders, J. Z., Kaiser, R. J., Hughes, P., Dodd, C., Connell, C. R., Heiner, C., Kent, S. B. H., Hood, L. E., 1986, Nature, 321, 674);

(ii) the use of ddNTPs tethered to detectable groups as terminators of DNA synthesis (Prober, J. M., Trainor, G. L., Dam, R. J., Hobbs, F. W., Robertson, C. W., Zagursky, R. J., Cocuzza, A. J., Jensen, M. A., Baumeister, K. 1987, Science, 238, 336, Lee, L. G., Connell, C. R., Woo, S. L., Cheng, R. D., McArdle, B. F., Fuller, C. W., Hallolan, N. D., Wilson, R. K., 1992, Nucleic Acids Res., 20, 2471);

(iii) the use mass spectrometry to analyse DNA fragments (Fizgerald, M. C., Zhu, L., Smith, L. M., 1993, Rapid Commun. Mass Spectrom., 7, 895).

The labeled dNTPs ought to be almost as good substrates to DNA polymerases as normal dNTPs. Since DNA polymerases are very sensitive to structural changes of their substrates, the selection of methods to attach non-radioactive markers into dNTPs are rather limited. It has already shown that the well-known terminators of DNA synthesis, 2',3'-dideoxy-3'-amino NTPs (Chidzeavadze, Z. G., Beabealashvilli, R. Sh., Anttrazhev, A. M., Kukhanova, M. K., Azhayev, A., Krayevsky, A. A., 1984, Nucleic Acids Res., 12, 1671) are not substrates of DNA polymerases when bulky reporter groups are attached to their 3'-amino function (Herrlein, M. K., Konrad, R. E., Engels, J. W., Holletz, T., Cech, D., 1994, Helv. Chim. Acta, 77, 586). Analogously, while 2'-amino-2'-deoxy-ara adenosine TP is an effective terminating substrate, introduction of bulky substituent to the 2'-position causes total loss of substrate properties of the molecule (Alexandriva, L. A., Sharkin, Yu. A., 1993, Collect. Czech. Chem. Commun. Spec. issue, 58, 113). These problems can be solved by attaching the label to 3'-position of the carbohydrate moiety in the end of a flexible tether arm (Hovinen, J., Azhayeva, E., Azhayev, A., Guzaev, A., Lönnberg, H., 1994, J. Chem. Soc. Perkin Trans 1, 211). In such manner the bulky reported group may be kept distant from the catalytic centre of the polymerase enzyme, while the base residues remain unmodified. Furthermore, the flexible arm should not severely restrict the conformational motion of the sugar ring upon binding to enzyme.

A method reported by Prober et al. (Prober, J. M., Trainor, G. L., Dam, R. J., Hobbs, F. W., Robertson, C. W., Zagursky, R. J., Cocuzza, A. J., Jensen, M. A., Baumeister, K. 1987, Science, 238, 336) consists of the preparation of ddNTPs bearing four different labels attached to their base moieties. Since their fluorescence spectra differ from each other all four terminating triphosphates can be used in a single sequencing reaction. The label is attached covalently to the nucleobase via a rigid propargylamine linker at C5 of the pyrimidine nucleosides and at C7 of 7-deazapurine nucleosides, e.g. at positions which are not involved in the formation of normal Watson-Crick base pairs. However, these label molecules used are organic dyes which suffer from commonly known drawbacks such as Raman scattering, concentration quenching and low water solubility.

A solid-phase method, called minisequencing, has been introduced for detection of point mutation of DNA (Syvänen, A.-C., Allto-Setälä, K., Harju, L., Söderlund, H., 1990, Genomics, 8, 684, Jalanko, A., Kere, J., Savilahti, E., Schwartz, M., Syvänen, A.-C., Söderlund, H., 1992, Clin. Chem, 38, 39) The method involves hybridization of immobilized single-stranded DNA with a primer that ends immediately before the site of mutation, and elongation of the chain with a single labeled deoxyriobonucleoside 5'-triphosphate. Parallel runs with each of the four possible nucleotides enable identification of the mutated base. Thus far, practically only radioactive detection methods have been used. Application of fluorescence techniques has been suffered from drawbacks such as low detection sensitivity and problems assosiated with the properties of the labeled triphosphates to act as good substrates for DNA polymerases.

The unique properties of lanthanide(III) chelates such as strong long-decay time luminescence make them ideal markers for numerous applications. Furthermore, large Stokes shift and very sharp emission bands enable the simultaneous use of four lanthanides (i.e. Eu, Tb, Sm, Dy) in the analysis. Time resolved fluorimetric assays based on lanthanide chelates have found increasing applications in diagnostics, research and high throughput screening. The heterogenous DELFIA technique (EP 0139675 B1; U.S. Pat. No. 4,808,541; EP 0298939 B1; U.S. Pat. No. 6,127,529; U.S. Pat. No. 4,565,790; WO 03/076939; Hemmilä I., Dakubu, S., Mukkala, V.-M., Siitari, H., Lövgren, T., 1984, Anal. Biochem. 137, 335; FI Pat. Appl. 20065030) is applied in assays requiring exceptional sensitivity, robustness and multi-label approach. The development highly stable and luminescent lanthanide(III) chelates (Hemmilä, I.; Mukkala, V.-M. 2001, Crit. Rev. Clin. Lab. Sci. 38, 441) has enabled the use of homogenous assay technologies based on time resolution.

The different photochemical properties of europium, terbium, dysprosium and samarium chelates enable development even multiparametric homogenous assays. Accordingly, a number of attempts have been made to develop new highly luminescent chelate labels suitable for time-resolved fluorometric applications. These include e.g. stabile chelates composed of derivatives of pyridines [U.S. Pat. No. 4,920,195; U.S. Pat. No. 4,801,722; U.S Pat. No. 4,761,481; PCT/FI91/00373; U.S. Pat. No. 4,459,186; EP A-0770610; Remuinan et al, J. *Chem. Soc. Perkin Trans* 2, 1993, 1099], bipyridines [U.S. Pat. No. 5,216,134], terpyridines [U.S. Pat. No. 4,859,777; U.S. Pat. No. 5,202,423; U.S. Pat. No. 5,324,825] or various phenolic compounds [U.S. Pat. No. 4,670,572; U.S. Pat. No. 4,794,191; Ital Pat. 42508 A789] as the energy mediating groups and polycarboxylic acids as chelating parts. In addition, various dicarboxylate derivatives [U.S. Pat. No. 5,032,677; U.S. Pat. No. 5,055,578; U.S. Pat. No. 4,772,563] macrocyclic cryptates [U.S. Pat. No. 4,927,923; WO 93/5049; EP-A-493745] and macrocyclic Schiff bases [EP-A-369000] have been disclosed. Recently, development of neutral, highly luminescent stable europium, terbium, samarium and dysprosium chelates based on azamacrocycles has been disclosed [U.S. patent application Ser. No. 10/928,143; U.S. patent application Ser. No. 11/004,061].

However, the use of lanthanide(III) chelates as reporter groups in terminating substrates for DNA polymerases has not been suggested in prior art.

SUMMARY OF THE INVENTION

The main object of the present invention is to provide nucleoside 5'-triphosphates or their acylic analogues labeled with luminescent or non-luminescent lanthanide(III) chelates to serve as terminating substrates for DNA polymerases. The major advantages of the present invention are:

(i) Each DNA nucleobase is detected by its own metal chelate, i.e. four bases (Ade, Gua, Cyt, Thy) and four metal chelates ($Eu^{3+}$, $Tb^{3+}$, $Sm^{3+}$, $Dy^{3+}$). Accordingly, the base sequence can be analyzed by detecting the specific signal derived form the appropriate lanthanide chelate.

(ii) The lanthanide(III) chelate can be either luminescent or non-luminescent. Accordingly, the structure of the chelate can be chosen to fulfil the requirements of the desired detection technology.

If the sequencing procedure includes electroporetic separation, it is desirable that the net charges of the terminating substrates do not differ from the natural 2'-deoxyribonucleoside 5'-triphosphates. In these cases, the use of neutral lanthanide chelates is advantageous.

Thus, the present invention concerns a terminating substrate for DNA polymerases of formula (I)

Z-R-L-X (I)

wherein,

Z is triphosphate anion or its organic or inorganic salt;

R is a recognizing moiety, which is a nucleoside comprising a base bound to a 2,3-dideoxyribose or its acyclic derivative; and Z-R has the formula (II)

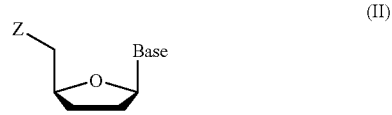

(II)

wherein the ribose ring optionally is replaced by an acyclic derivative in which one or both of the 2- and 3-carbon atoms from the ribose ring optionally are missing;

-L- is a linker; and

X is a lanthanide(II) chelate.

According to another aspect, the invention concerns the use of the terminating substrate according to claim 1 in DNA sequencing for determining the base sequence wherein each base is identified by detecting the signal derived from the lanthanide chelate of said terminating substrate.

DETAILED DESCRIPTION OF THE INVENTION

The base in the recognizing moiety R is adenine, guanine, cytosine, thymine or uracil. Also modifications of said bases can be used. As preferable modifications can be mentioned 7-deaza-adenine and 7-deazaguanine.

In case the ribose ring is replaced by an acyclic derivative of said ring, a preferable acyclic derivative is the dimethyl ether bridge derived from the ribose ring.

In case Z as defined above is an organic or inorganic salt of triphosphate, the salt is most preferably sodium, lithium, potassium, calcium, magnesium, ammonium tributylammonium ortriethylammonium salt.

According to a preferable embodiment, the recognizing moiety R is a radical selected from the following seven structures;

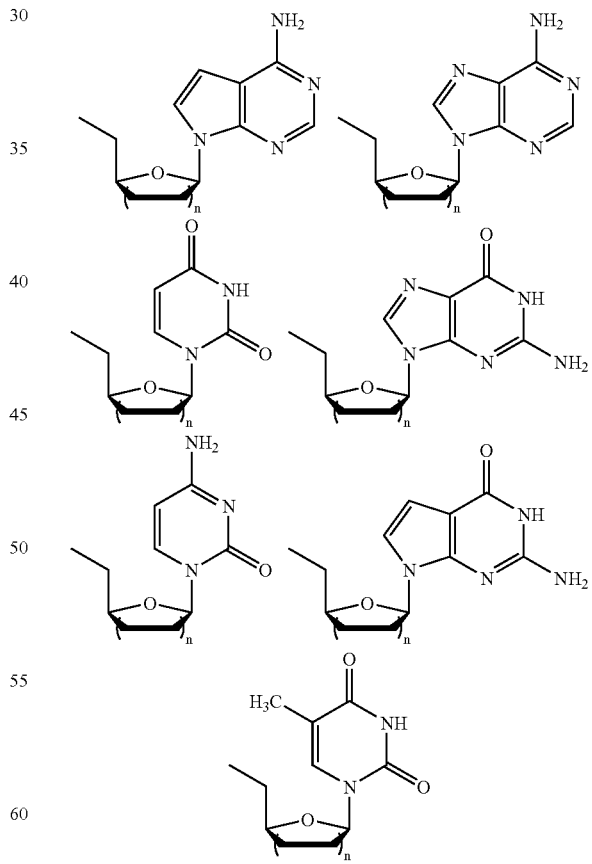

where n is 0 or 1.

According to a preferable embodiment, the linker -L- is connected to C7 of 7-deazaadenine, C7 of 7-deazaguanine, C5 of cytosine, C5 of uracil, C3' of 2'-deoxyguanosine, C3'

2'-deoxyadenosine, C3' of 2'-deoxycytidine or C3' of thymidine. The linker is preferably formed from one to ten moieties, each moiety being selected from the group consisting of phenylene, alkyl containing 1-12 carbon atoms, ethynediyl (—C≡C—), ethylenediyl (—C═C—); ether (—O—), thioether (—S—), amide (—CO—NH— and —NH—CO— and —CO—NR' and —NR'—CO—), carbonyl (—CO—), ester (—COO— and —OOC—), disulfide (—SS—), diaza, (—N═N—), thiourea (—NH—CS—NH—) or a tertiary amine (—NR'—), where R' represents an alkyl containing less than 5 carbon atoms.

According to a preferable embodiment, the lanthanide chelate X is either luminescent or non-luminescent, and the lanthanide(III) ion is selected in such a way that each DNA nucleobase referes to one lanthanide(III) ion.

Although any luminescent or non-luminescent lanthanide (III) chelate is suitable as reporter group in the terminating substrate according to the present invention, the lanthanide chelates disclosed in the Background section above are preferable. Particularly preferable lanthanide(III) chelates for this purpose are luminescent chelates based on triazacycloalkanes and nonluminescent chelates based on pyridine-2,6-diyl-bis (methylenenitrilo)tetrakis(acetic acid).

EXPERIMENTAL SECTION

The invention is further elucidated by the following non-restricting examples. The structures and synthetic routes employed in the experimental part are depicted in Scheme 1. Experimental details are given in Example 1. Scheme 2 discloses an example on the synthesis procedure for the preparation of a terminating substrate for DNA polymerase labeled with a highly luminescent dysprosium chelate via a tether at the carbohydrate moiety. Syntheses of the starting materials are given by reference. Capture of the biotinylated oligonucleotides to the solid support is described in Example 2. Minisequencing reaction and analysis is described in Example 3.

Procedures

Biotinylated oligonucleotides and detection primer were purchased from Sigma-Genosys. Poymerase Pol B, dilution buffer, reaction buffer and acycloterminators were products of NEN. Streptavidin coated microtiter plates, assay buffer, wash buffer, enhancement solution, DELFIA Enhancer and lanthanide chelates were from PerkinElmer Life and Analytical Sciences. Minisequencing assays were analyzed with Victor multilabel counter (Wallac Oy, PerkinElmer Life and Analytical Sciences).

EXAMPLE 1

Synthesis of the Labeled Triphosphates

The acycloterminators tethered to propargylamino groups, 1a-d, were allowed to react with lanthanide(III) chelates of 2,2',2'',2'''-[[4-[(4-isothiocyanatophenyl)ethyl)]pyridine-2, 6-diyl]bis(methylenenitrilo)]tetrakis(acetic acid) 2a-d under slighly basic conditions (pyridine:water:triethylamine; 3:1:0.06; v/v/v) overnight at ambient temperature. After precipitation from acetone, the crude products, 3a-d were redissolved in water and purified on HPLC techniques (column: Inertsil ODS-3, RP-18; Buffer A: 0.05 M ammonium acetate; Buffer B: A in 50% (v/v) acetonitrile; gradient: from A to 60% B in 30 min; flow rate was 1 mL·min$^{-1}$). Characterization was performed on MALDI-TOF mass spectrometry. In all the cases the spectra were in accordance with the proposed structures.

EXAMPLE 2

Capture of Biotinylated Oligonucleotides on the Solid Support

Biotinylated oligonucleotides (6 pmol/well in 40 μL) were captured on streptavidin coated microtiter plates in 30 min by shaking at RT. To remove unbound templates wells were rinsed 4 times with wash buffer.

EXAMPLE 3

Minisequencing Reactions and Analysis

Reaction mixture (40 μl) contained the detection primer (0.5-5 pmol/well), polymerase Pol B (0.1 U/well) and lanthanide chelate labeled acycloterminator (3a-d). The amount of the triphosphates depended on the lanthanide chelate and was as follows. The amount of Eu-GTP and Tb-UTP was 0.5 pmol/well and both Sm-ATP and Dy-CTP was 50 pmol/well. The reaction was allowed to proceed with shaking 20 minutes at 68° C. After the reactions wells were rinsed 6 times with wash buffer.

Analysis of reaction was performed according to DELFIA protocol using Victor Multilabel Counter. Shortly, lanthanide ions were released to solution with enhancement solution (200 μl) and shaking 25 minutes, and in the case of Tb and Dy additional 5 min after the addition of 50 μl DELFIA Enhancer. Luminescent chelates formed during this period of time were measured with Victor Multilabel counter. All four acycloterminators labeled with different lanthanide ions, 3a-d, were found to incorporate specifically to primers. Totally unoptimized reactions gave 3.6, 1.4, 1.7 and 1.4 times higher specific signals over nonspecific signals for Eu, Tb, Sm and Dy, respectively.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

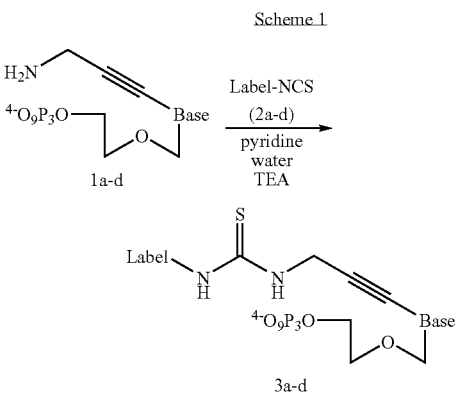

Scheme 1

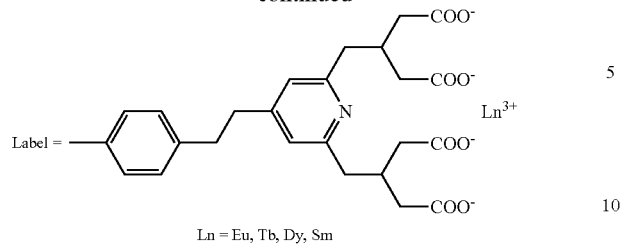
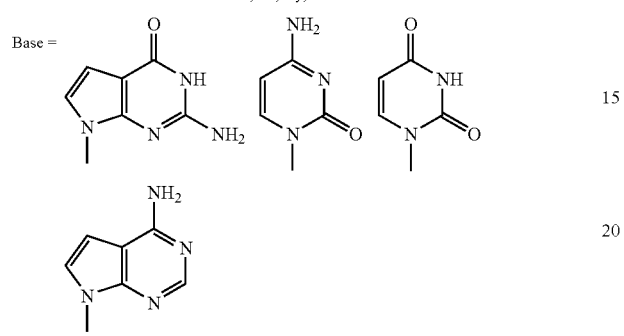
Scheme 2
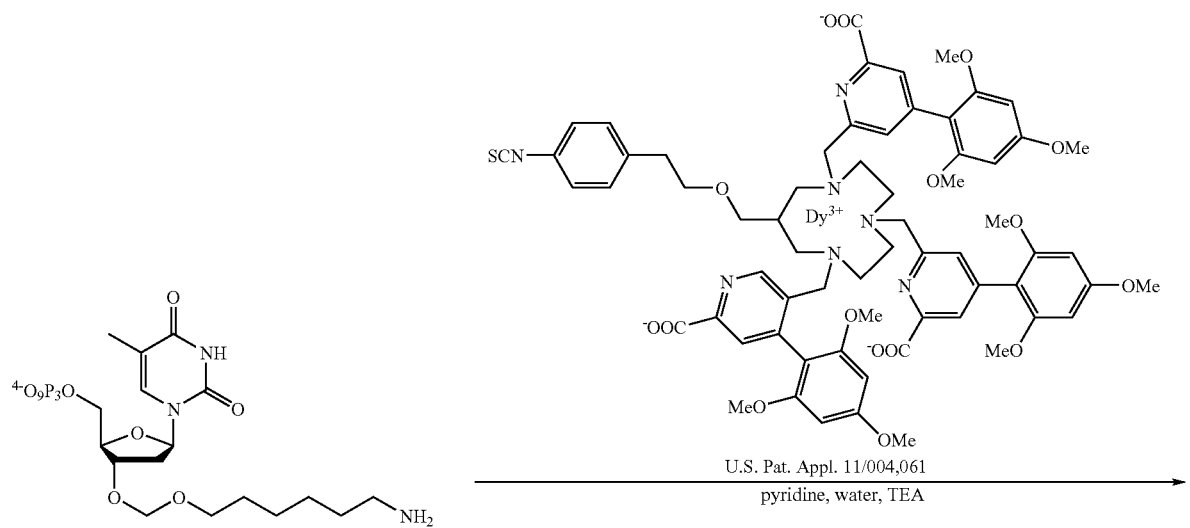
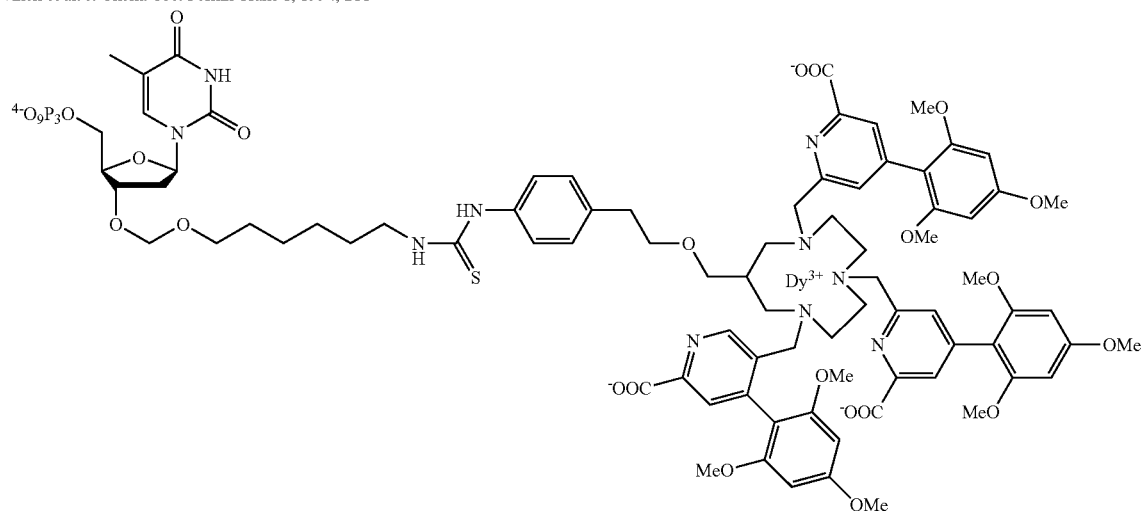

The invention claimed is:

1. A molecule of formula (I)

Z-R-L-X (I)

wherein,

Z is a triphosphate anion or its organic or inorganic salt;

R is a recognizing moiety, which is a nucleoside comprising a base bound to a 2,3-dideoxyribose or its acyclic derivative; and Z-R has the formula (II)

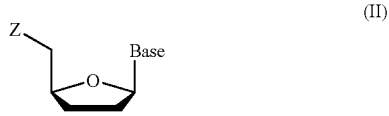

wherein the ribose ring optionally is replaced by an acyclic derivative in which one or both of the 2- and 3-carbon atoms from the ribose ring optionally are missing;

-L- is a linker; and

X is a non-luminescent lanthanide(III) chelate comprising a lanthanide(III) ion, wherein the lanthanide(III) ion is selected from the group consisting of europium, terbium, dysprosium and samarium.

2. The molecule according to claim 1, wherein Z is an organic or inorganic salt of triphosphate.

3. The molecule according to claim 1, wherein the recognizing moiety is a radical derived from the following seven structures:

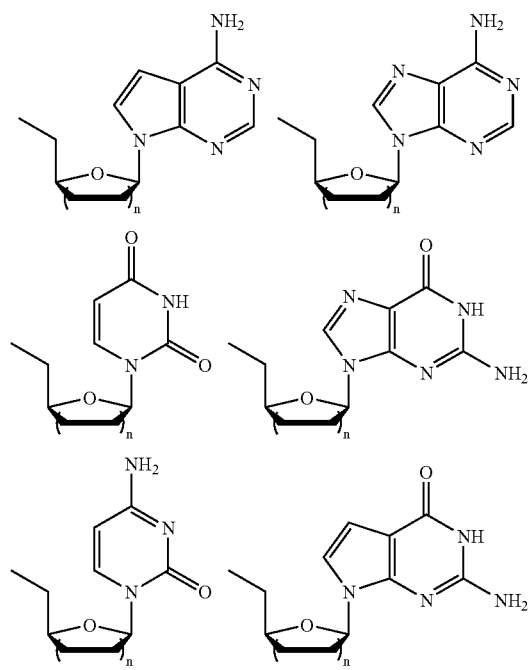

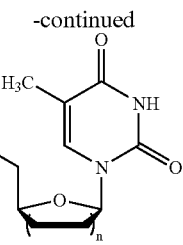

where n is 0 or 1.

4. The molecule according to claim 1, wherein the linker -L- is connected to one or more of C7 of 7-deazaadenine, C7 of 7-deazaguanine, C5 of cytosine, and C5 of uracil.

5. The molecule according to claim 1, wherein:

the linker -L- is formed from one to ten moieties;

each of said one to ten moieties selected from the group consisting of phenylene, alkyl containing 1-12 carbon atoms, ethynediyl (—C≡C—), ethylenediyl (—C=C—); ether (—O—), thioether (—S—), amide (—CO—NH— or —NH—CO— or —CO—NR' or —NR'—CO—), carbonyl (—CO—), ester (—COO— or —OOC—), disulfide (—SS—), diaza, (—N=N—), thiourea (—NH—CS—NH—) and a tertiary amine (—NR'—), wherein R' represents an alkyl containing less than 5 carbon atoms.

6. The molecule according to claim 1, wherein the non-luminescent lanthanide(III) chelate has the following structure:

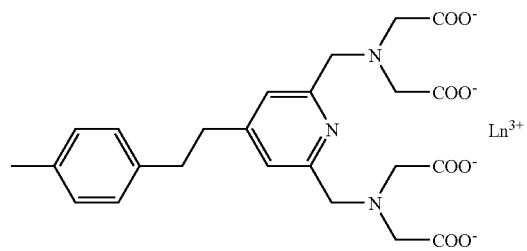

wherein Ln is selected from the group consisting of europium, terbium, dysprosium and samarium.

7. A method of sequencing DNA, comprising:

(a) performing a sequencing reaction in the presence of a molecule of claim 1; and (b) detecting a signal derived from the non-luminescent lanthanide(III) chelate of the molecule of claim 1, thereby identifying a base of a DNA sequence.

8. The method according to claim 7, wherein guanine is detected by the signal of europium, thymine is detected by the signal of terbium, adenine is detected by the signal of samarium and cytosine is detected by the signal of dysprosium.

9. The molecule according to claim 2, wherein said organic or inorganic salt of trephosphate is selected from the group consisting of a sodium, a lithium, a calcium, a potassium, a magnesium, an ammonium tributylammonium and a triethylammonium salt.

* * * * *